US011097103B2

(12) United States Patent
Straka et al.

(10) Patent No.: US 11,097,103 B2
(45) Date of Patent: Aug. 24, 2021

(54) SENSOR BAND FOR MULTIMODAL SENSING OF BIOMETRIC DATA

(71) Applicant: Myant Inc., Toronto (CA)

(72) Inventors: Adrian Straka, Toronto (CA); Jiwon Yang, Toronto (CA); Parth Jain, Toronto (CA); Mark Klibanov, Toronto (CA); Michelle Zheng, Toronto (CA); Gabriel Stefan, Toronto (CA); Monica Nealis, Toronto (CA); Milad Alizadeh-Meghrazi, Toronto (CA)

(73) Assignee: MYANT INC., Toronto (CA)

( * ) Notice: Subject to any disclaimer, the term of this patent is extended or adjusted under 35 U.S.C. 154(b) by 0 days.

(21) Appl. No.: 16/001,499

(22) Filed: Jun. 6, 2018

(65) Prior Publication Data
US 2018/0345015 A1 Dec. 6, 2018

Related U.S. Application Data

(63) Continuation-in-part of application No. 15/615,035, filed on Jun. 6, 2017, now abandoned.

(51) Int. Cl.
A61N 1/36 (2006.01)
A61B 5/00 (2006.01)
(Continued)

(52) U.S. Cl.
CPC .......... *A61N 1/36031* (2017.08); *A41B 9/001* (2013.01); *A41D 1/002* (2013.01);
(Continued)

(58) Field of Classification Search
CPC ................ A61N 1/025; A61N 1/36031; A61N 1/36003; A61N 1/0452; A61N 1/0456;
(Continued)

(56) References Cited

U.S. PATENT DOCUMENTS

| 4,919,148 A * | 4/1990 | Muccio ............... A61N 1/0452 607/152 |
| 2002/0138125 A1* | 9/2002 | Axelgaard ......... A61B 5/04085 607/149 |

(Continued)

FOREIGN PATENT DOCUMENTS

WO 2017075703 A1 5/2017

OTHER PUBLICATIONS

Chen, Yun Hsuan et al. "Soft, Comfortable Polymer Dry Electrodes for High Quality ECG and EEG Recording." Sensors (Switzerland) 14.12 (2014): 23758-23780. Sensors (Switzerland). Web.*

(Continued)

Primary Examiner — Allen Porter
Assistant Examiner — James Moss
(74) Attorney, Agent, or Firm — Norton Rose Fulbright Canada LLP

(57) ABSTRACT

A resilient fabric band providing a sensor platform for a wearer in order to sense a plurality of biometric data, the band comprising: a pair of ECG sensors coupled to an interior surface of a body of the band, each of the pair of ECG sensors located on either side of a front to back centerline of the body; a pair of bio impedance sensors coupled to the interior surface of the body of the band, each of the pair of bio impedance sensors located on either side of the front to back centerline; a strain gauge sensor coupled to the body of the band; a computer device mounted on the body of the band via a housing, the computer device including a power source, a computer processor, a memory for storing instructions for execution by the computer processor, and a network interface for transmitting data sensed by the sensors; and a plurality of communication pathways connecting the computer device to each of the sensors, the communication pathway for sending power from the power (Continued)

supply to the sensors as controlled by the computer processor and for receiving sensed data from the sensors by the computer processor.

6 Claims, 11 Drawing Sheets

(51) Int. Cl.
| | |
|---|---|
| *A44B 9/00* | (2006.01) |
| *A41D 1/00* | (2018.01) |
| *A61B 5/0205* | (2006.01) |
| *A61B 5/01* | (2006.01) |
| *A61B 5/053* | (2021.01) |
| *A61N 1/02* | (2006.01) |
| *A61B 5/11* | (2006.01) |
| *A61N 1/04* | (2006.01) |
| *A61B 5/16* | (2006.01) |
| *A61B 5/282* | (2021.01) |

(52) U.S. Cl.
CPC .......... *A61B 5/0205* (2013.01); *A61B 5/6804* (2013.01); *A61N 1/36003* (2013.01); *A41B 2400/32* (2013.01); *A61B 5/01* (2013.01); *A61B 5/02055* (2013.01); *A61B 5/053* (2013.01); *A61B 5/1118* (2013.01); *A61B 5/165* (2013.01); *A61B 5/282* (2021.01); *A61B 2562/0219* (2013.01); *A61B 2562/0261* (2013.01); *A61B 2562/043* (2013.01); *A61B 2562/063* (2013.01); *A61N 1/025* (2013.01); *A61N 1/0452* (2013.01); *A61N 1/0456* (2013.01); *A61N 1/0484* (2013.01)

(58) Field of Classification Search
CPC .................. A61N 1/0484; A61B 5/053; A61B 2562/063; A61B 2562/0219; A61B 2562/0261; A61B 5/02055; A61B 5/04085; A61B 2562/043; A61B 5/01; A61B 5/0205; A61B 5/6804; A61B 5/165; A61B 5/1118; A41B 2400/32; A41B 9/001; A41D 1/002
See application file for complete search history.

(56) References Cited

U.S. PATENT DOCUMENTS

| | | | | |
|---|---|---|---|---|
| 2005/0012490 | A1 | 6/2005 | Misczynski | |
| 2005/0124901 | A1* | 6/2005 | Misczynski | A61B 5/02438 |
| | | | | 600/509 |
| 2005/0177059 | A1* | 8/2005 | Koivumaa | A61B 5/0488 |
| | | | | 600/546 |
| 2007/0299325 | A1* | 12/2007 | Farrell | A61B 5/0002 |
| | | | | 600/301 |
| 2008/0097530 | A1* | 4/2008 | Muccio | A61N 1/0452 |
| | | | | 607/3 |
| 2008/0143080 | A1* | 6/2008 | Burr | D04B 1/14 |
| | | | | 280/495 |
| 2009/0076364 | A1 | 3/2009 | Libbus et al. | |
| 2011/0270115 | A1 | 11/2011 | Streeter | |
| 2013/0192071 | A1* | 8/2013 | Esposito | A61B 5/1036 |
| | | | | 33/6 |
| 2014/0065107 | A1* | 3/2014 | Lockwood | A61N 1/321 |
| | | | | 424/93.7 |
| 2014/0070957 | A1 | 3/2014 | Longinotti-Buitoni | |
| 2016/0095527 | A1 | 4/2016 | Thng et al. | |
| 2016/0128632 | A1* | 5/2016 | Wiebe | A61B 5/0015 |
| | | | | 340/870.07 |
| 2016/0256104 | A1 | 9/2016 | Romem et al. | |
| 2016/0324442 | A1 | 11/2016 | Zdeblick | |
| 2016/0331974 | A1* | 11/2016 | Lyons | A61N 1/36003 |
| 2017/0036066 | A1 | 2/2017 | Chahine | |
| 2017/0056644 | A1 | 3/2017 | Chahine et al. | |

OTHER PUBLICATIONS

"Electroactive Polymers", https://en.wikipedia.org/wiki/Electroactive_polymers. Wikipedia. Viewed on May 4, 2019.*

Cadenius E and Gartvall K. "Next generation of active underwear—Implementing smart textiles and technologies.", Master of Science Thesis, KTH Industrial Engineering and Management, Sweden, 2015, http://www.diva-portal.org/smash/get/diva2:840137/FULLTEXT01.pdf, viewed on Mar. 9, 2018.*

S. Corbellini and A. Vallan, "Arduino-based portable system for bioelectrical impedance measurement," 2014 IEEE International Symposium on Medical Measurements and Applications (MeMeA), Lisboa, 2014, pp. 1-5. doi: 10.1109/MeMeA.2014.6860044, https://ieeexplore.ieee.org/document/6860044.*

International Search Report and Written Opinion, dated Sep. 4, 2018, in PCT Patent Application No. PCT/CA2018/000113.

Office Action, dated Aug. 7, 2018, in U.S. Appl. No. 15/615,035.

USPTO, Office Action for U.S. Appl. No. 15/615,035 dated Sep. 5, 2019.

USPTO, Office Action for U.S. Appl. No. 15/615,035 dated Mar. 19, 2019.

Cadenius E and Gartvall K. "Next generation of active underwear—Implementing smart textiles and technologies.", Master of Science Thesis, KTH Industrial Engineering and Management, Sweden, 2015, http://www.diva-portal.org/smash/get/diva2:840137/FULLTEXT01.pdf, viewed Mar. 9, 2019.

S. Corbellini and A. Vallan, "Arduino-based portable system for bioelectrical impedance measurement," 2014 IEEE International Symposium on Medical Measurements and Applications (MeMeA), Lisboa, 2014, pp. 1-5. doi: 10.1109/MeMeA.2014.6860044, https://ieeexplore.ieee.org/document/6860044, viewed Mar. 9, 2019.

Farooq, Muhammad & Sazonov, Edward. (2015). Strain Sensors in Wearable Devices. 10.1007/978-3-319-18191-2_9, https://www.researchgate.net/publication/300796983_Strain_Sensors_in_Wearable_Devices, viewed on Mar. 12, 2019.

Hermann Scharfetter et al., "Fat and hydration monitoring by abdominal bioimpedance analysis: data interpretation by hierarchical electrical modeling," in IEEE Transactions on Biomedical Engineering, vol. 52, No. 6, pp. 975-982, Jun. 2005.

EPO, Extended European Search Report for EP Application No. 18814272.3 dated Jan. 19, 2021.

\* cited by examiner

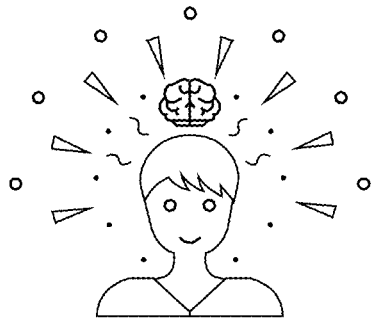

Improve your State of Mind

Detect what makes you stressed, and use our app to get you back into the right state of mind. SKIIN's smart notiifcations can remind you to breathe after a sressful event, and cope with the things life throws at you.

43

Optimize Sleep

If you're constantly tired in the mornings, it's probably related to the efficiency of your sleep. SKIIN uses the most advanced sensors located on the waistband of the garment to accurately track your sleep. Wake up feeling refreshed.

43

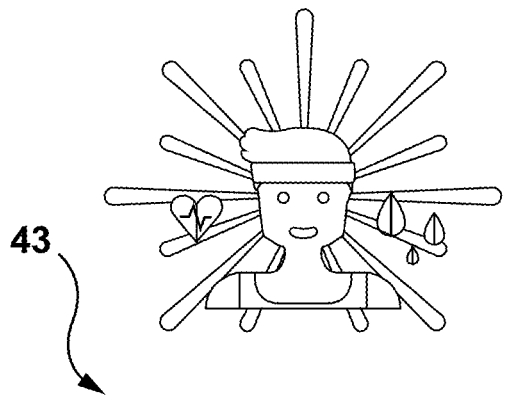

Be Active, Feel Better

Being active is important to your physical and mental health. SKIIN can tell you if you're spending enough time on your feet. taking enough steps, and keeping your posture upright.

43

Control your Home

Your smart home should react to you: not the other way around. Use SKIIN to control your thermostat. lights and speakers based on your mood and body temperature.

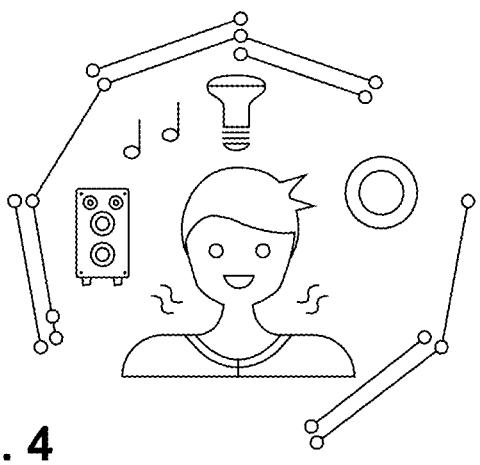

SENSOR BAND FOR MULTIMODAL SENSING OF BIOMETRIC DATA

CROSS-REFERENCE TO RELATED APPLICATIONS

This application is a continuation-in-part of U.S. patent application Ser. No. 15/615,035, filed on Jun. 6, 2017; the entire contents of which are hereby incorporated by reference herein.

FIELD

The present disclosure relates to sensing systems for biometric data.

BACKGROUND

Sensing of biometric data in today's technological based environment is key to understanding the physical state. In particular, athletes and medical patients, among a number of other consumers, are key individuals for much needed accurate and up-to-date (i.e. real-time) biometric sensing. However, state of the art sensor arrangements can be bulky and uncomfortable for the typical wearer. Further, each physical activity and/or health condition can require a customized sensor arrangement and mode of attachment to the wearer, which can unnecessarily require multiple sensor platforms tailored to each individual/disease.

SUMMARY

It is an object of the present invention to provide a biometric sensing platform to obviate or mitigate at least one of the above presented disadvantages.

An aspect provided is a resilient fabric band providing a sensor platform for a wearer in order to sense a plurality of biometric data, the band comprising: a pair of ECG sensors coupled to an interior surface of a body of the band, each of the pair of ECG sensors located on either side of a front to back centerline of the body; a pair of bio impedance sensors coupled to the interior surface of the body of the band, each of the pair of bio impedance sensors located on either side of the front to back centerline; a strain gauge sensor coupled to the body of the band; a computer device mounted on the body of the band via a housing, the computer device including a power source, a computer processor, a memory for storing instructions for execution by the computer processor, and a network interface for transmitting data sensed by the sensors; and a plurality of communication pathways connecting the computer device to each of the sensors, the communication pathway for sending power from the power supply to the sensors as controlled by the computer processor and for receiving sensed data from the sensors by the computer processor.

A further aspect provided is a resilient fabric band providing a sensor platform for a body of a wearer in order to sense biometric data, the band comprising: a computer device mounted on the body of the band via a housing, the computer device including a power source, a computer processor, a memory for storing instructions for execution by the computer processor, and a network interface for transmitting data sensed by the sensors; and a plurality of communication pathways connecting the computer device to each of the sensors, the communication pathway for sending power from the power supply to the sensors as controlled by the computer processor and for receiving sensed data from the sensors by the computer processor; and an electromuscular stimulator sensor of the sensors, the electro-muscular stimulator sensor positioned in a respective location of at least one side of a centerline of the band running from front to back with respect to the body of the wearer of the band.

BRIEF DESCRIPTION OF THE DRAWINGS

The foregoing and other aspects will now be described by way of example only with reference to the attached drawings, in which:

FIG. 4 shows example applications of the biometric data combinations;

DETAILED DESCRIPTION

Figure 1:
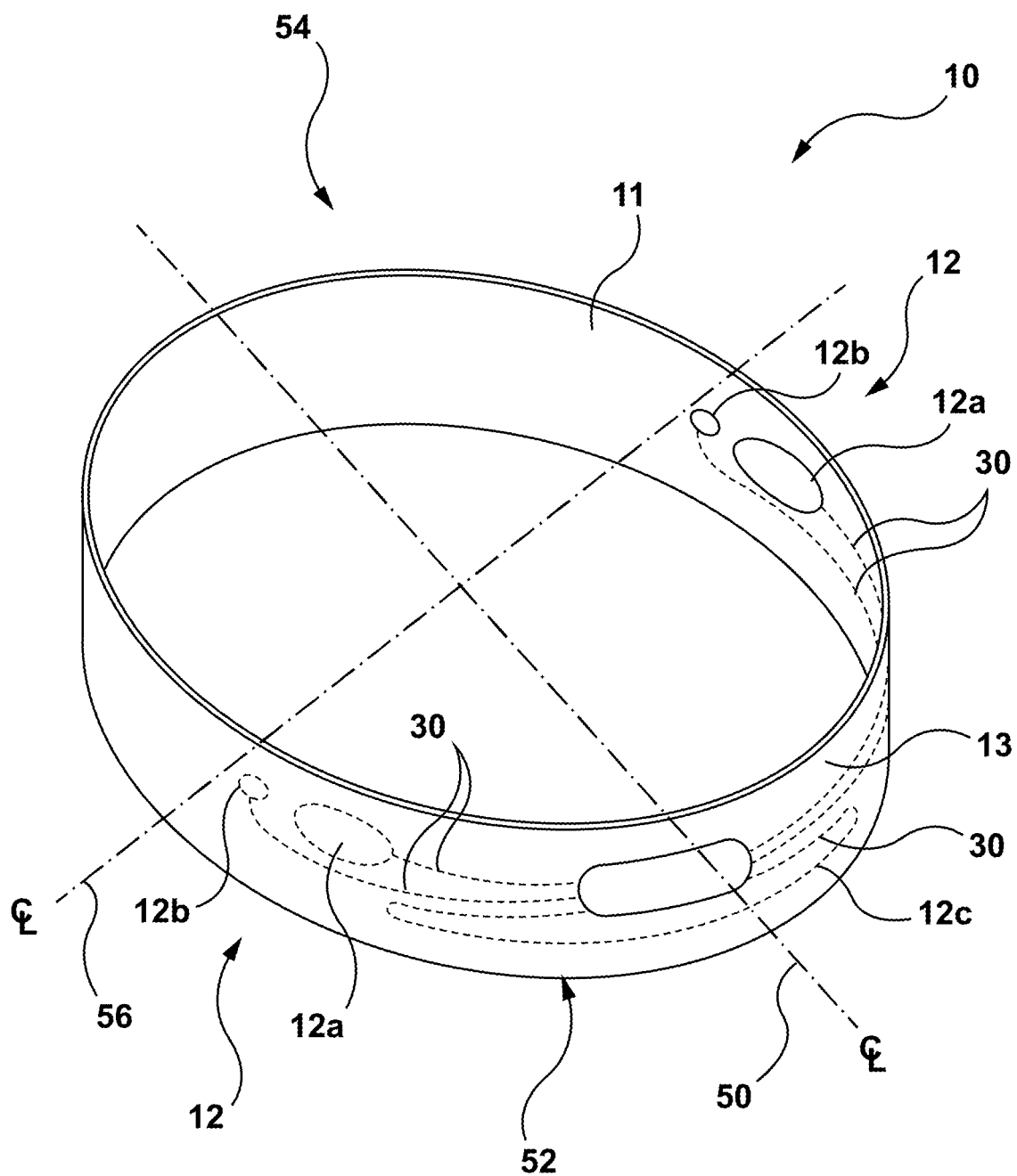
FIG. 1 is a perspective view of a band containing a plurality of sensors.

Referring to FIG. 1, shown is a fabric band 10, preferable having a resilient knit type, for fitting around a body part of a wearer (not shown), in order to collect different modes/types of biometric data based on the type/number of sensors 12 positioned either on or otherwise knit/woven (e.g. embroidered) into the fabric making up the body of the band 10. It is recognised that the body part can be such as but not limited to: waist or abdomen; limb such as a leg or arm; torso/trunk; buttocks; foot or ankle; wrist or hand; and/or head. The fabric band 10 can be provided as a stand-alone article or can be combined/combined into an article of clothing such as but not limited to: underwear 11 (see FIG. 2—such as but not limited to any type of undergarment including jockey shorts, panties, undershirts, and bras); socks, limb bands (e.g. knee band); shirt (e.g. undershirt); etc. In terms of combined into an article of clothing (i.e. garment 11), the band 10 can be formed as an integral component of the interlacing of the fibres making up the garment 11. The fabric of the body of the band 10 can be comprised of interlaced resilient fibres (e.g. stretchable natural and/or synthetic material and/or a combination of stretchable and non-stretchable materials).

Referring again to FIG. 1, provided as distributed about the band 10, e.g. mounted on an interior surface 111 (i.e. inward facing towards the body of the wearer), are a series of sensors/electrodes 12 including ECG sensors 12a, bio impedance sensors 12b, and strain gauge sensors 12c. It is recognised that the sensors 12 can be composed of Electroactive polymers, or EAPs, and/or woven or knit plurality of conductive fibres constructed in a sensor/electrode configuration (e.g. a patch).

Also positioned on the band 10, for example on an exterior surface 13 (i.e. outward facing from the wearer), is series of electrical components 15 including a computer device 14 (see FIG. 3) including a computer processor 16, a memory 18 for executing stored instructions for receiving and processing of data obtained from the sensors 12, as well as communicating via a network interface 20 with a network 22 (e.g. Wi-Fi, Bluetooth, attached wired cable, etc.) as well as sending and receiving electrical signals from the sensors 12. The processor 16, memory 18 and network interface 20 are mounted on a printed circuit board 26, which is housed in a housing 24 attached to the band 10. Also connected to the PCB 24 is a temperature sensor 12d for measuring a body temperature of the wearer. Also mounted in the housing is a power supply 28 (e.g. battery) for powering the various electrical components 15 within the housing 24 as well as the sensors 12a,b,c external to the housing 24, connected via conductive communication pathways 30 (e.g. wires—see FIG. 1—woven into the fabric weave/knit of the band 10 textile). The pathways 30 can be coupled to the sensors 12 via use of a conductive grommet, as desired. Also provided is a series of motion sensors 36 (e.g. accelerometer(s) and gyroscopes) for determining movements of the wearer, including posture as further described below. The sensors 12 can also be provided as speaker/microphone (e.g. for auditory signals/communication with the wearer), illumination sensors (e.g. LEDS—for visual signals/communication with the wearer) and haptic/vibrations sensors (e.g. actuators—for motion/touch signals/communication with the wearer).

Sensor Examples

The sensors 12 can be composed of Electroactive polymers, or EAPs, which are polymers that exhibit a change in size or shape when stimulated by an electric field. EAPS could also exhibit a change in electrical field if stimulated by mechanical deformation. The most common applications of this type of material are in actuators and sensors. A typical characteristic property of an EAP is that they will undergo deformation while sustaining forces. For example, EPDM rubber containing various additives for optimum conductivity, flexibility and ease of fabrication can be used as a sensor 12 material for measuring electrode impedance measured on human skin of the wearer. Further, EAPs may be used to measure ECG as well as measuring deformation (i.e. expansion of the waist and therefore breathing can be inferred from EAPs). ECG can be measured using surface electrodes, textile or polymer, as desired.

These electrodes 12 can be capable of recording biopotential signals such as ECG while for low-amplitude signals such as EEG, as coupled via pathways 30 with an active circuit of the electrical components 15 within the housing 24. The ECG sensors 12a can be used to collect and transmit signals to the computer processor 16 reflective of the heart rate of the wearer. AS such, it is recognized that the electrodes as sensors 12 can be composed of conductive yarn/fibres (e.g. knitted, woven, embroidery using conductive fibres—e.g. silver wire/threads) of the band 10, as desired.

In terms of bioelectrical impedance, these sensors 12a,b and their measurements can be used in analysis (BIA) via the processor 16 and memory 18 instructions for estimating body composition, and in particular body fat. In terms of estimating body fat, BIA actually determines the electrical impedance, or opposition to the flow of an electric current through body tissues of the wearer interposed between the sensors 12 (e.g. 12a,b), which can then be used to estimate total body water (TBW), which can be used to estimate fat-free body mass and, by difference with body weight, body fat.

In terms of strain sensing, these sensors 12c can be operated as a strain gauge to take advantage of the physical property of electrical conductance and its dependence on the conductor's geometry. When the electrical conductor 12c is stretched within the limits of its elasticity such that it does not break or permanently deform, the sensor 12c will become narrower and longer, changes that increase its electrical resistance end-to-end. Conversely, when the sensor 12c is compressed such that it does not buckle, the sensor 12c will broaden and shorten, changes that decrease its electrical resistance end-to-end. From the measured electrical resistance of the strain gauge, via the power 28 that is administered to the sensors 12 via the computer processor 16 acting on stored 18 instructions, the amount of induced stress can be inferred. For example, a strain gauge 12c arranged as a long, thin conductive fibres in a zig-zag pattern of parallel lines such that a small amount of stress in the direction of the orientation of the parallel lines results in a multiplicatively larger strain measurement over the effective length of the conductor surfaces in the array of conductive lines—and hence a multiplicatively larger change in resistance—than would be observed with a single straight-line conductive wire. In terms of location/structure of the strain gauge 12c, the strain gauge can be located around the circumference of the band 10. A further embodiment is where the strain gauge 12c is located in a portion of the circumference, for example in a serpentine arrangement, positioned in a front 52 portion (positioned adjacent to the front of the wearer) of the band 10. The strain gauge 12c can be configured for sensing in the k Ohm range.

In terms of temperature sensor 12d, this sensor is used to measure the dynamic body temperature of the wear. For example, the temperature sensor 12d can be a thermistor type sensor, which is a thermally sensitive resistors whose prime function is to exhibit a large, predictable and precise change in electrical resistance when subjected to a corresponding change in body temperature. Examples cam include Negative Temperature Coefficient (NTC) thermistors exhibiting a decrease in electrical resistance when subjected to an increase in body temperature and Positive Temperature Coefficient (PTC) thermistors exhibiting an increase in electrical resistance when subjected to an increase in body temperature. Other temperature sensor types can include thermocouples, resistance thermometers and/or silicon bandgap temperature sensors as desired. It is also recognized that the sensors 12 can include haptic feedback sensors that can be actuated via the computer processor 16 in response to sensed data 44 processed onboard by the processor 16 and/or instructions received from a third party device 60 or the wearer (operator of the computer device 40) via an interface 20. Another example of temperature sensors 12d is where thermocouples could be knitted into the band 10 fabric using textile and coupled directly to the body of the wearer through close proximity/contact in order to get more accurate temperature readings.

Sensed Data and Processing

Referring again to FIGS. 2 and 3, the processor 16 (acting on stored 18 instructions) can transmit the collected data 44 (in raw format and/or in preprocessed format from the sensors 12) to an external computer device 40 (e.g. smartphone or other desktop application) for viewing and/or further processing of the sense data. For example, the device 40 application can display the sensed data 44 in a dashboard type format 46 on a display 42 (or other type of GUI interface) for viewing by the wearer (or by another person other than the wearer that has been provided access to the data 44). For example, the sensed data 44 can be provided in a dashboard format indicating real-time (or other selected dynamic periodic frequency) of: body temperature for indicating fluctuations in skin temperature; gyroscope/accelerometer measurements for indicating amount/degree of physical activity (i.e. via sensed motion) of the wearer as well as contributing via gyroscope readings of wearer posture (for example in the case where the band 10 is positioned at the waist of the wearer) as well as determined calculation of number of calories expended; strain gauge measurements (e.g. via conductive yarn) in order to indicate real-time breathing of the wearer as the band 10 expands and contracts as well as the ability to differentiate strain degree contributing to posture angle (i.e. band and associated strain sensor 12c with change in length as the posture of the wearer changes due to bending at the waist—in the case of the underwear 11 example of FIG. 2); real-time heart rate measurements based on sensed ECG data using the sensors 12a; and real-time hydration/body fat measurements based on galvanic sensing using the sensors 12b (and optionally 12a as further described below).

It is recognised that multiple sources of sensed data (e.g. temperature sensor 12d with activity/motion sensors 36 can be used in an algorithm stored in memory 18 to calculate calories expended based on activity combined with body temperature). Other combinations of sensed data types can include combinations such as but not limited to: heart rate with activity data; heart rate with activity data with temperature; activity data with bio impedance data; strain gauge for breathing rate data determination with activity data and heart rate data for determination of exertion levels; etc. It is also realized that combinations of sensor type readings can be used by the computer processor 16 to determine exercise activity type being performed by the wearer, based on computer models of activity type with typical sensor data, for example gradual changes in body posture with detected lower levels of heart rate and breathing could be indicative of a wearer practicing yoga. A further type of multiple sensed data usage can be for accelerometer and gyroscope data, such that both can be used or one can be used and the other discounted during determination of a selected metric of the dashboard 46. For example, in the case of the band 10 being situated at the waist of an overweight person, the "off-vertical" reading of the gyroscope would not be indicative of a bent posture (from the vertical), rather due to the folded waistband due to body composition. As such, the degree of gyroscope readings would be discounted from the calculation of the posture determination.

Referring again to FIG. 1, the location of the sensors 12a,b are such that they are positioned in pairs on either side of a centerline 50, in order to position an appropriate amount of body mass between the sensors 12a,b as well as providing an appropriate conductive path through the body of the wearer (e.g. cross body measurement). It is also recognised that placement of the sensors 12a,b are preferred in body regions where muscle noise (actions of muscles can introduce signal noise into the adjacent sensors 12) is minimized. As such, the sensors 12a,b can be positioned in the band 10 in a location for positioning adjacent to the hip and/or the kidney of the wearer in the case where the band 10 is positioned at the waist. It is recognised that positioning the sensors 12a,b in the band 10 in order to be adjacent to either hip of the wearer, i.e. both sensors 12a,b of the pair to one side of the centerline 56 of the band 10, would provide for a lower signal amplitude/quality when wearer activity is subdued (e.g. resting) however would also advantageously provide an increases signal quality when the wearer is active (as the presence of utilized muscle mass adjacent to the hip region is minimal as compared to other regions about the waist).

It is also recognised that location of the sensors 12a,b can be positioned to either side of the centerline 50 running front to back rather than to either side of the centerline 56 running side to side (of the wearer), as the separation distance for the typical wearer is greater side to side rather than front to back (i.e. wider between hips verses between spine and belly button).

Further, one example option for the sensor configuration is a 4-electrode ECG sensor configuration. Cost of such an ECG design can be a factors however the design could potentially give better signal performance. The theory behind the four sensor ECG design is that the processor 16 can switch between each sensor pair (of the multiple pair ECG sensor configuration) to find the one with the best signal quality and use that one during sensed movement of the wearer.

Referring again to FIG. 3, the processor 16 and associated stored 18 instructions can be used to determine (based on received sensor 12 readings) bio impedance values by utilizing both of the ECG sensors 12a and the sensors 12b at the same time. This is advantageous as EGC sensing (using sensors 12a) cannot occur at the same time as bio impedance sensing (using sensors 12b), as signal amplitude generated by the sensors 12b oversaturates the EGC sensors 12a. As such, it is recognised that the processor 16 cycles between ECG readings and bio impedance readings (i.e. these readings are done sequentially rather than in parallel). As such, the processor instructs power to both the sensors 12a,b on one side of the centerline 50 as drivers and both the sensors 12a,b on the other side of the centerline 50 as collectors during taking of bio impedance readings. As such, it is recognised that the positioning of the sensor pair 12a and the sensor pair 12b can be symmetrical about the centerline(s) 50,56.

Figure 3:
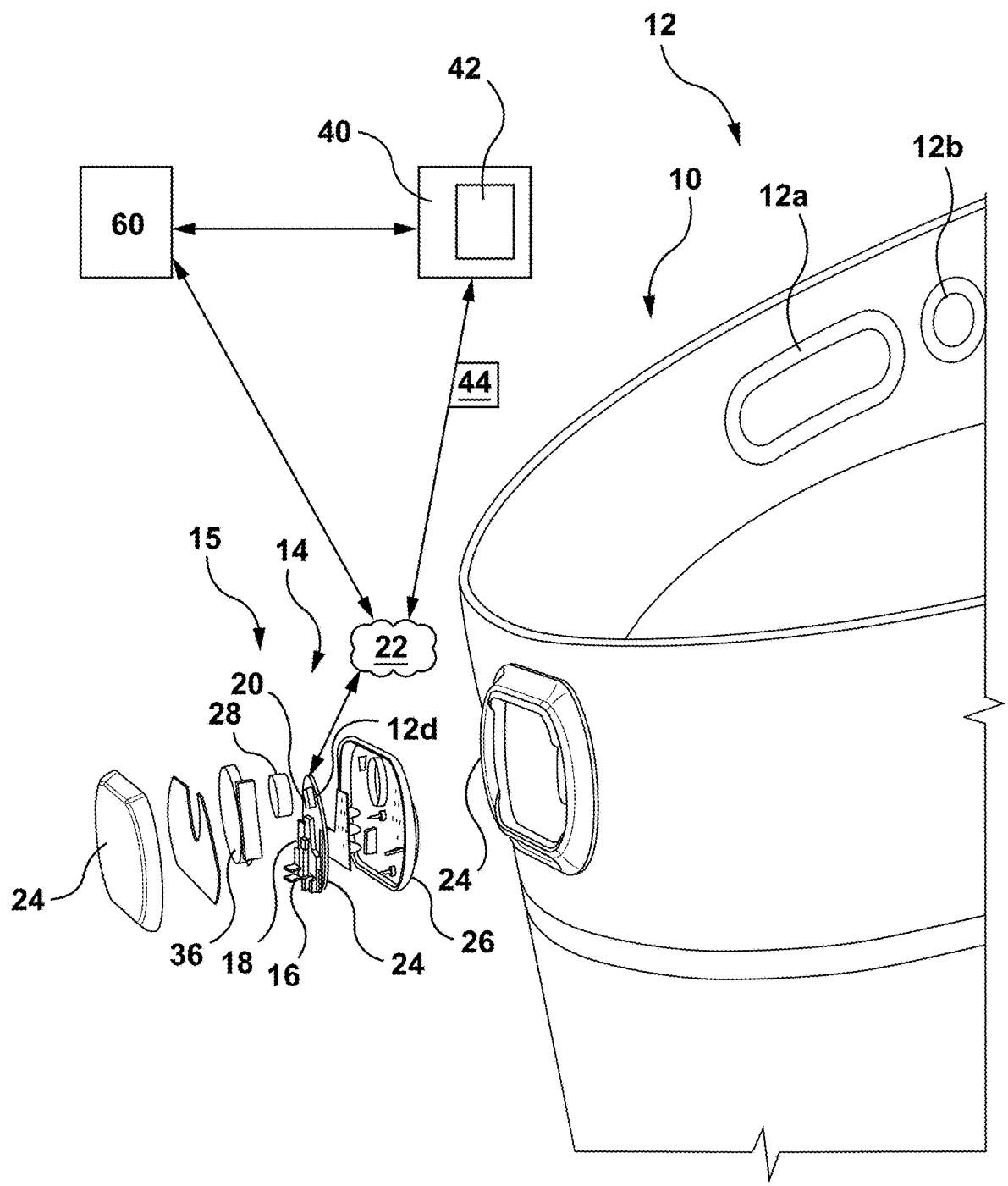
FIG. 3 shows an embodiment of the band shown in FIG. 1 with associated electrical components.

Referring to FIGS. 3 and 4, the computer device 14 can be used to send the sensed data 44 to the off band computer device 40, which can then use its own customized applications 43 to process the sensed data 44 to inform the wearer of their physical/mental state on potential adaptations/changes that can be actively done by the wearer. For example, the application 43 can report sensed data 44 pertaining to a combination of temperature and activity over time as an indicator of the quality of sleep of the wearer. Further, the application 43 can notify the wearer of a determined emotional state of the wearer (e.g. based on a combination of breathing data and activity data—with optional ECG data) as well as continued monitoring of the data combination to inform the wearer whether steps taken by the wearer are positively influencing the determined emotional state. Further, the application 43 can track and report on the degree as well as quality/nature of the wearer's activity, for example based on a combination of strain gauge data and activity data. Further, the application can interact with other external computer networked devices 60 (see FIG. 3) such as but not limited to music systems, heating system, lighting systems, etc in response to a determined mood and/or temperature of the wearer based on a combination of sensed data (e.g. activity, heartrate, etc.).

Figure 5:
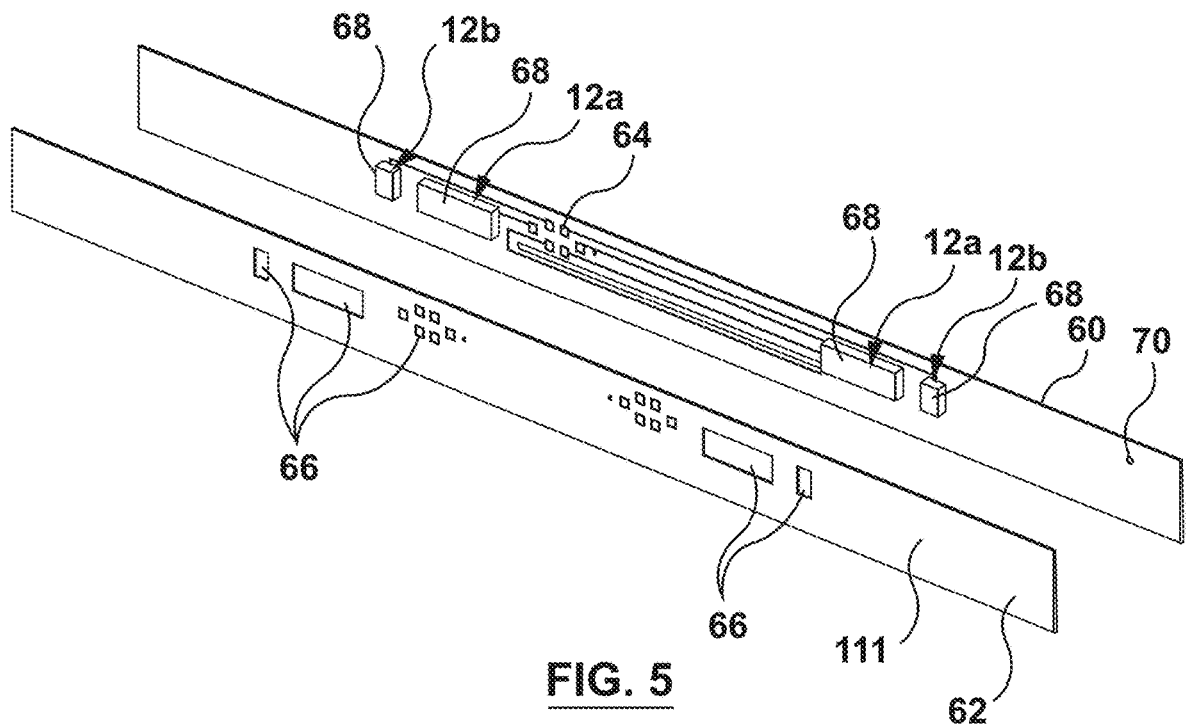
FIG. 5 shows a front perspective view of a further embodiment of the band of FIG. 1.
Figure 6:
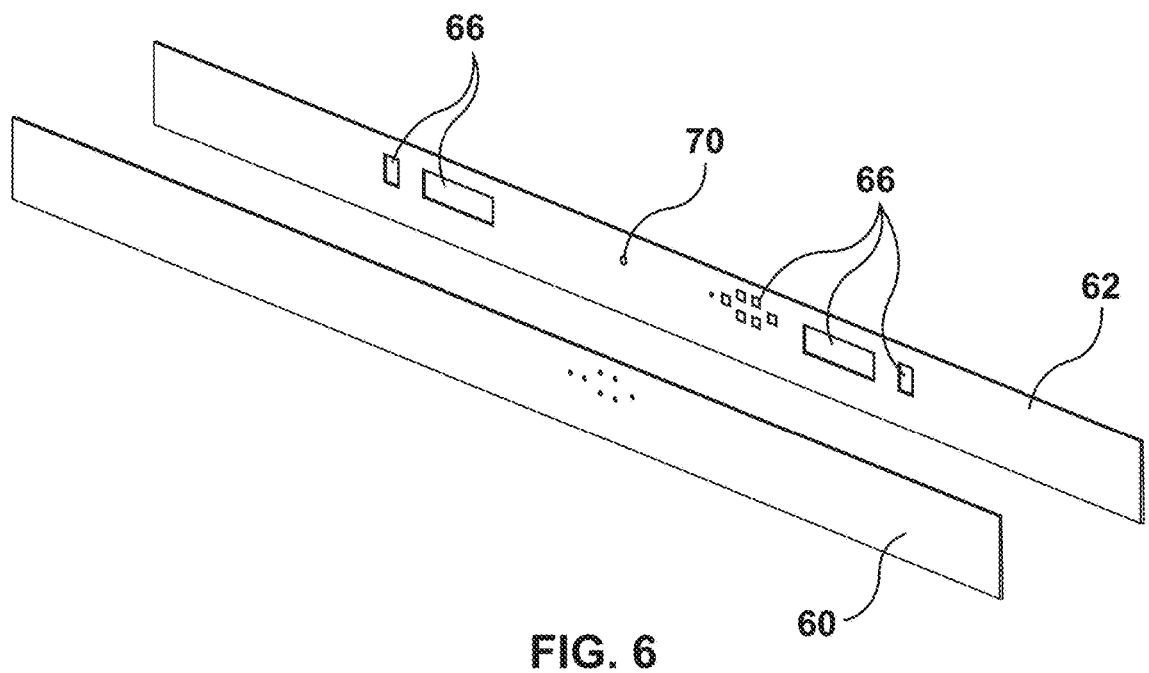
FIG. 6 shows a rear perspective view of the further embodiment of FIG. 5.

Referring to FIGS. 5 and 6, shown is an alternative embodiment of the band 10, in exploded view. In particular, the band 10 is composed of a front band portion 60 and a back band portion 62, such that the portion 60 has sensors 12a,b with communication pathways 30 electrically connecting the sensors 12a,b to respective connectors 64 (which connect to respective connector portions of the PCB 26 (see FIG. 3), in order to electrically couple the sensors 12a,b to the network interface 20). The band portion 62 has cutouts 66 in order for the sensors 12a,b to be received in the cutouts 66 when the band portions 60,62 are assembled with one another (e.g. coupled together for example by stitching via adjacently places surfaces 70), thus providing for surfaces 68 of the sensors 12a,b to become in contact with the skin of the wearer, as the surface 111 is for contact with the skin. It is recognized that the electrically conductive pathways 30 can be electrically conductive fibres interlaced with electrically insulative fibres comprising the material of the band portion 60.

Figure 7:
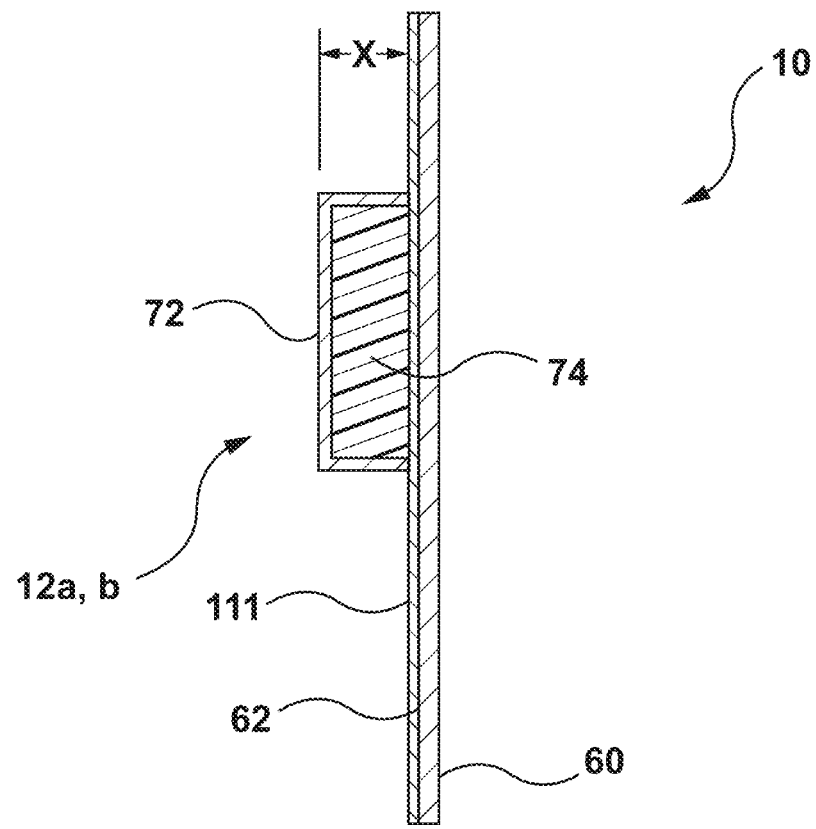
FIG. 7 shows a side view of the sensors mounted on the band of FIG. 5.

Referring to FIG. 7, shown is an example side view of one of the sensors 12a,b, such that the portions 60,62 are assembled and the sensors 12a,b are received in the cutouts 66 (see FIGS. 5,6). It is important to note that the sensors 12a,b themselves extend from the skin contact surface 111 by a distance X, thus providing for improved contact with the skin of the wearer. In particular, the sensors 12a,b can have a conductive portion 72 of the surface 68 (i.e. coupled to the communication pathways 30 extending through backing material 74) as well as the raised backing material 74 to provide for the respective extension of the conductive portion 72 of the sensors 12a,b from the surface 111. For example, the backing material 74 can be comprised of electrically insulative interlaced fibres interleaved with the textile fibres incorporating the material (i.e. electrically insulative fibres) of the band portion 62.

Figure 8:
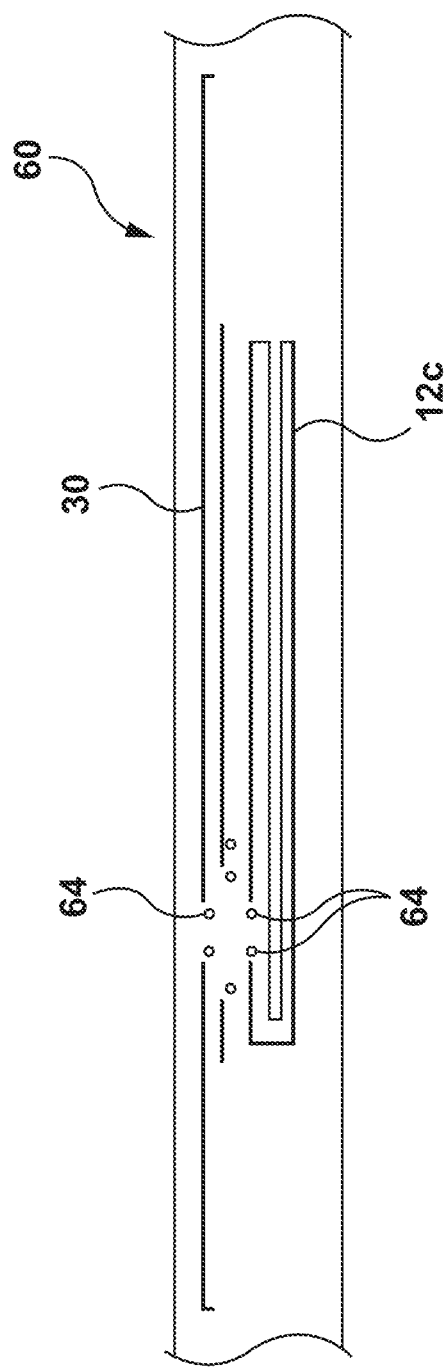
FIGS. 8 and 9 show further embodiments of the sensors of FIG. 1.
Figure 9:
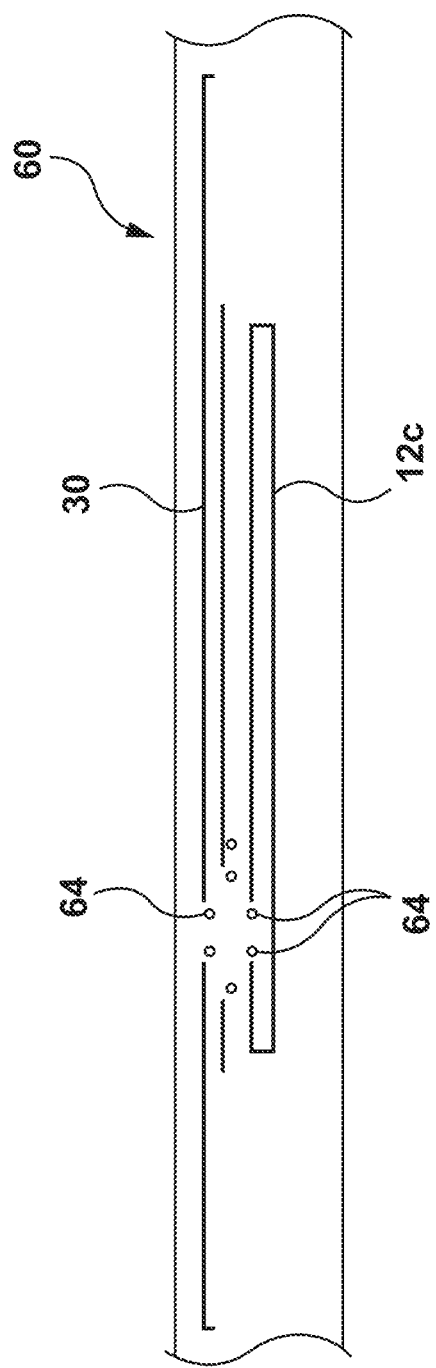

Referring to FIG. 8, shown is a further embodiment of the band portion 60 showing the strain gauge sensor 12c woven/knit in a serpentine fashion with other insulative fibres comprising the material of the band portion 60. As such, as shown in FIG. 7, it is recognized that once assembled, the band portion 62 would cover the strain gauge sensor 12c and thus insulate the skin of the wearer from direct contact with the electrically conductive fibres of the strain sensor 12c. FIG. 9 shows a further geometrical configuration of the strain sensor 12c.

Referring to FIGS. 5 to 8, it is recognized that they contain example geometrical layouts of the communication pathways 30 (e.g. traces) and the strain sensor 12c itself. The shown construction of the sensors 12a,b,c and band portions 60,62 are advantageous, as the entire pattern (of pathways 30 and sensor(s) 12c) is actually contained within covering portions 60,62 as one assembled (e.g. interlaced) layer of fabric, however the traces (of pathways 30 and sensor(s) 12c) are knitting inside the knit pattern and therefore as a consequence of that are insulated, therefore inhibiting any necessity of external insulation (glues, laminates, etc), in order to inhibit undesirably application of electrical charge from the traces to the skin of the wearer. Further, the 3D shape (e.g. extension from the surface 111) of the sensors 12a,b themselves can improves the sensors 12a,b contact with the skin and can provide for the collection of biometric data across a variety of skin conditions, dry or wet.

Figure 2:
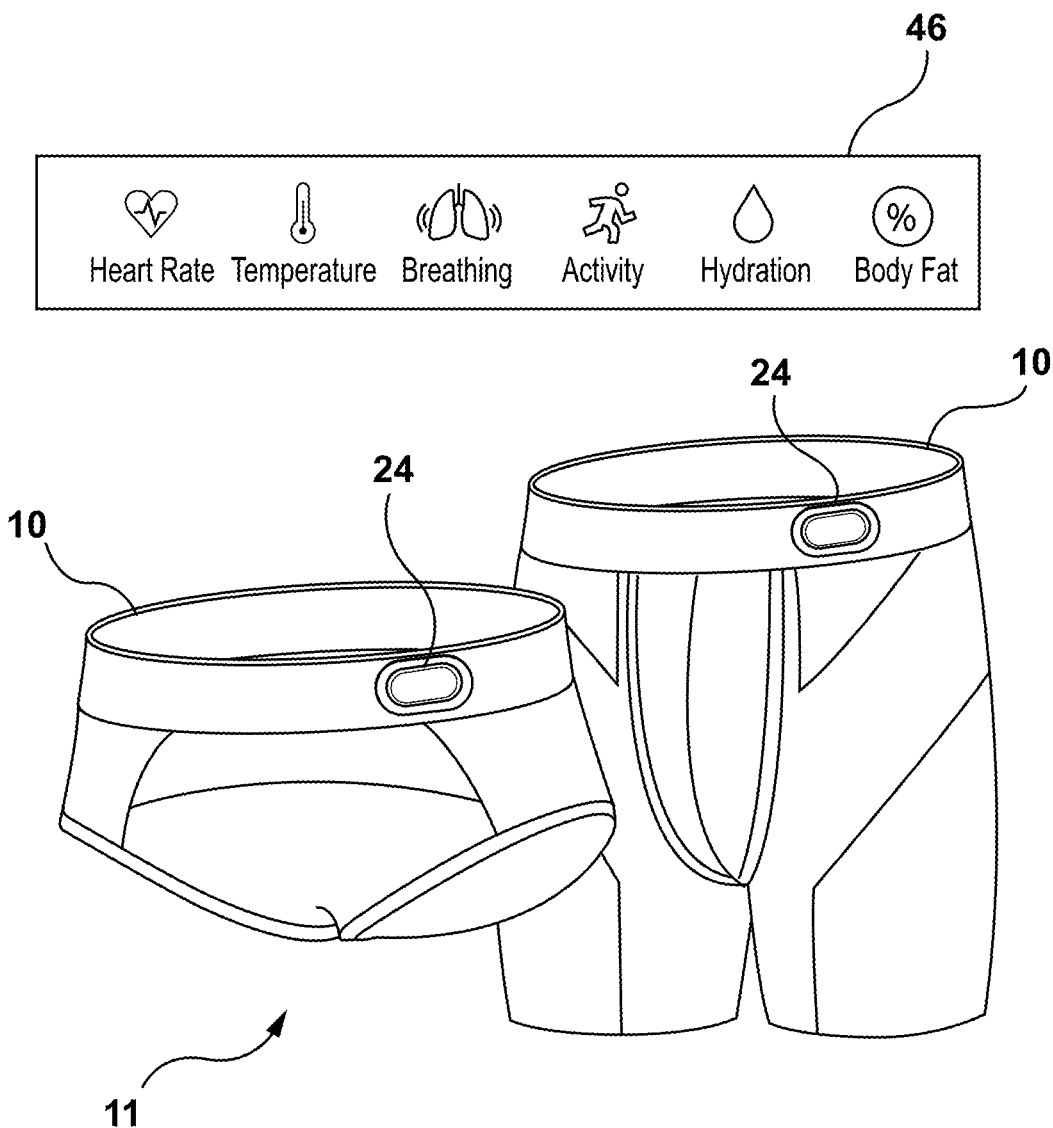
FIG. 2 is a view of the band shown in FIG. 1 incorporated into an article of clothing.
Figure 10:
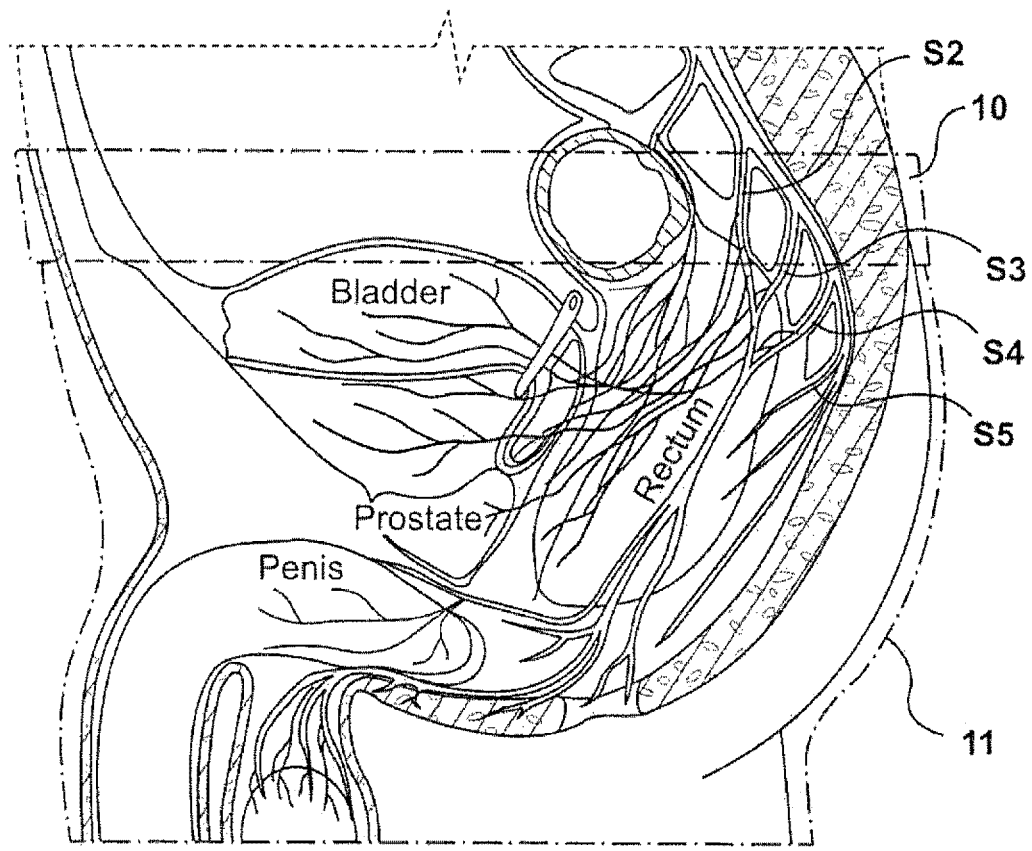
FIG. 10 shows an example side view of a body of a wearer of the band of FIG. 1.

Referring to FIGS. 2 and 10, shown is a body 8 of a wearer of the underwear 11 garment. The body 8 shows the location of the stimulating the pelvic splanchnic nerve sacral nerve (S2-S4), which can be stimulated via electro-muscular stimulator sensors/actuators 12 (as part of the platform of sensors/actuators 12) positioned in the textile of the garment 11, and as such coupled to the sensor band 10 (see FIGS. 1 and 10 in ghosted view) via communication pathways 30 in the textile of the garment 11 for sending and receiving electrical signals with respect to the PCB 26 (via the operation of the processor 16 and memory 18 in generation of electrical stimulation signals for the actuating the electro-muscular stimulator sensors/actuators 12 located adjacent to the pelvic splanchnic nerve sacral nerve (S2-S4), as part of the textile fabric of the underwear 11 by example. For example, the actuation of the electro-muscular stimulator sensors/actuators 12 located adjacent to the pelvic splanchnic nerve sacral nerve(s) (S2-S4) can be for the treatment of erectile dysfunction, as stimulation of the pelvic splanchnic nerve/sacral nerve (S2-S4) can be used to recover and treat erectile dysfunction. As per FIG. 10, the pelvic splanchnic nerves or nervi erigentes are splanchnic nerves that arise from sacral spinal nerves S2, S3, S4 to provide parasympathetic innervation to the hindgut. The pelvic splanchnic nerves S2, S3, S4 arise from the anterior rami of the sacral spinal nerves S2-S4 and enter the sacral plexus. They travel to their side's corresponding inferior hypogastric plexus, located bilaterally on the walls of the rectum.

Figure 11:
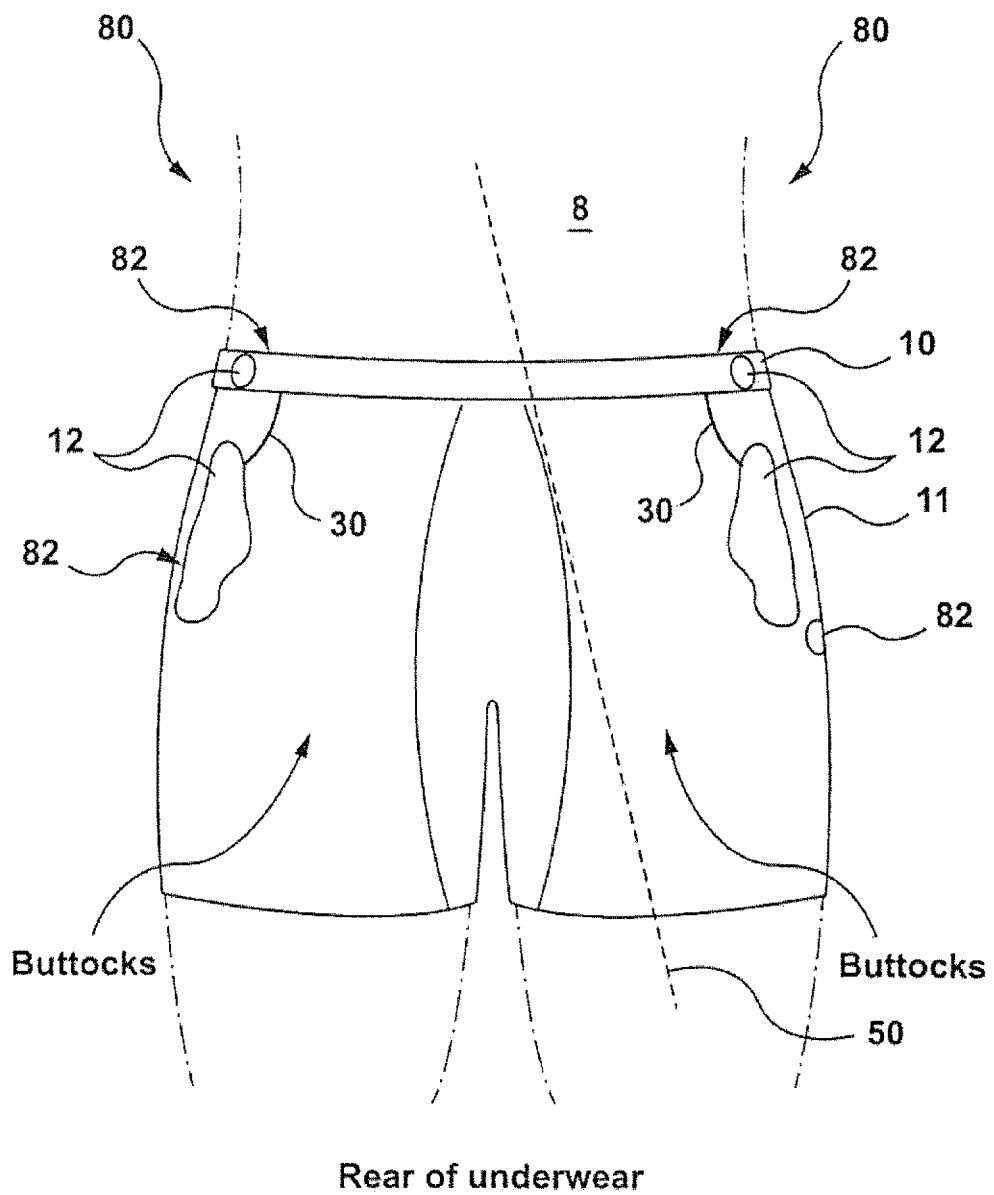
FIG. 11 shows a perspective rear view of an example garment incorporating the band of FIG. 1.

As shown in FIG. 11, by example is/are placement location(s) 82 for the electro-muscular stimulator sensors/actuators 12 located adjacent to the pelvic splanchnic nerve sacral nerve (S2-S4) location(s), i.e. located at and/or below the band 10 to one/either side 80 from the centerline 50 running from the front to the back of the garment 11 (i.e. from the front to the back of the patient's body 8). These location(s) 82 provide for positioning of the electro-muscular stimulator sensors/actuators 12 in the fabric of the garment 11, as adjacent to the body 8 locations of the pelvic splanchnic nerves S2, S3, S4 (see FIG. 10).

As discussed above, the electro-muscular stimulators (i.e. actuators) 12 are for applying an electrical stimulation signal (e.g. a shock) to the skin and underlying muscles of the wearer adjacent to the electro-muscular stimulators 12. It is recognized that the electro-muscular stimulators 12 are positioned in the location(s) 82, such that one or both of the electro-muscular stimulators 12 can be present in the location(s) 82 of the textile fabric of the band 10 and/or garment 11. The electro-muscular stimulator 12 positioned in the location(s) 82 (e.g. for positioning to either side of the centerline 50) can be used to receive electrical stimulation signals from the controller (as operate by the processor and memory) for application of the electrical stimulation signals as propagated to the sensors 12 via the communication pathways 30. The controller can be embodied as a computer device including the computer processor, the memory for executing stored instructions for receiving and processing of data obtained from the sensors 12, as well as sending and receiving electrical signals from the sensors 12. The processor, memory and network interface can be mounted on a printed circuit board, which is housed in a housing of the controller, as attached to the housing.

Electrical Stimulation fibres of the sensors 12 can provide/receive a seamless and pain-inhibited electrical pulse to/from the skin as a new modality of sensation via textiles. The electrical simulation proficient yarn/fibres can be incorporated in garments 11 on desired locations via and operated via a low (i.e. appropriate) current signal administered via the controller 14 and associated data processing system. For example, electrical pulses can be transmitted to the skin, which can invoke a tactile sensation, either from or to the wearer via the signals. The sensors 12 can be composed of Electroactive polymers, or EAPs, which are polymers that exhibit a change in size or shape when stimulated by an electric field. EAPS could also exhibit a change in electrical field if stimulated by mechanical deformation. The most common applications of this type of material are in actuators and sensors. A typical characteristic property of an EAP is that they will undergo deformation while sustaining forces. For example, EPDM rubber containing various additives for optimum conductivity, flexibility and ease of fabrication can be used as a sensor 18 material for measuring electrode impedance measured on human skin of the wearer. Further, EAPs may be used to measure ECG as well as measuring deformation (i.e. expansion of the waist and therefore breathing can be inferred from EAPs). ECG can be measured using surface electrodes, textile or polymer, as desired.

Figure 12:
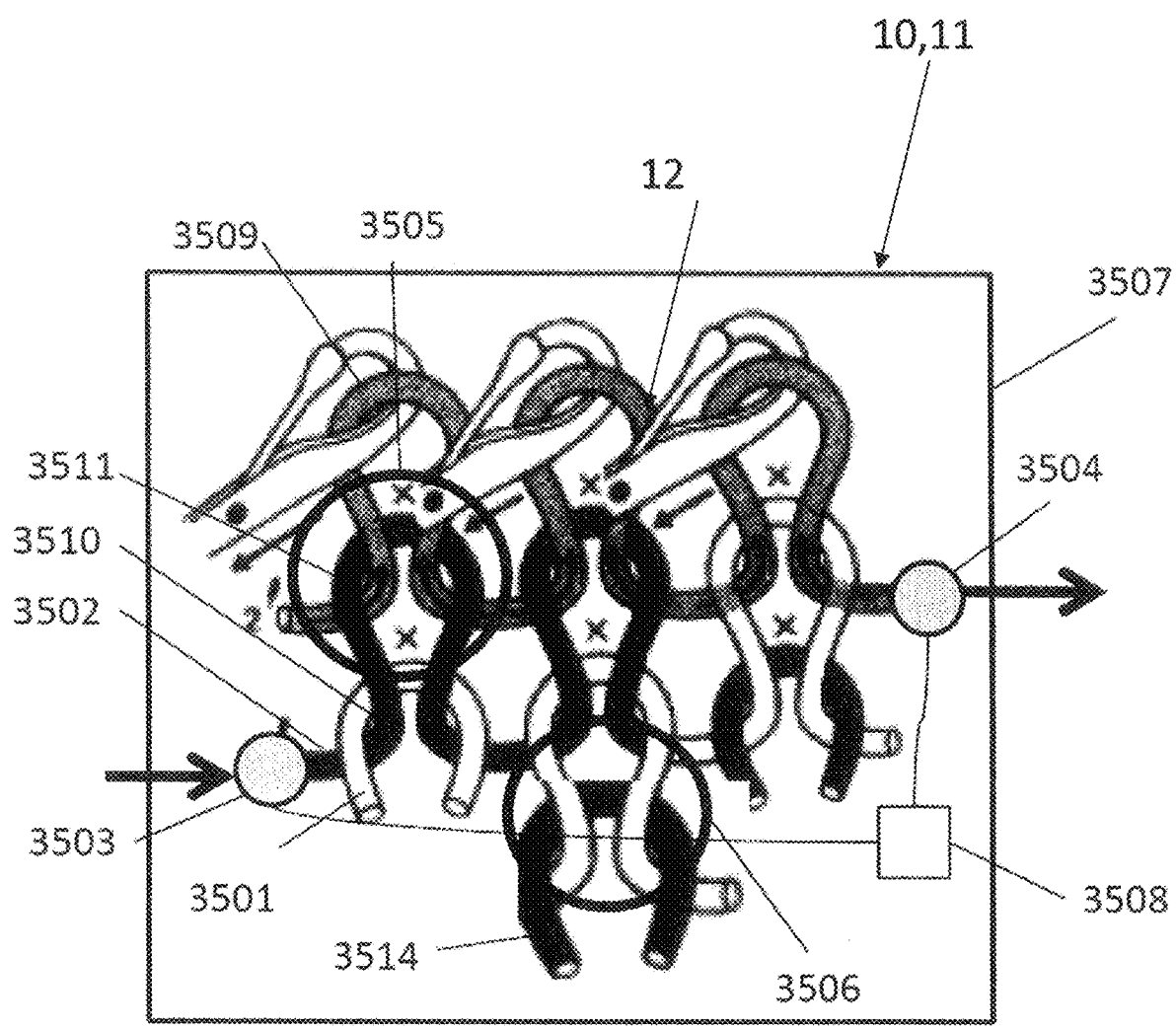
FIGS. 12 and 13 show example stitching patterns for the fabric of the band and garment of FIG. 2.
Figure 13:
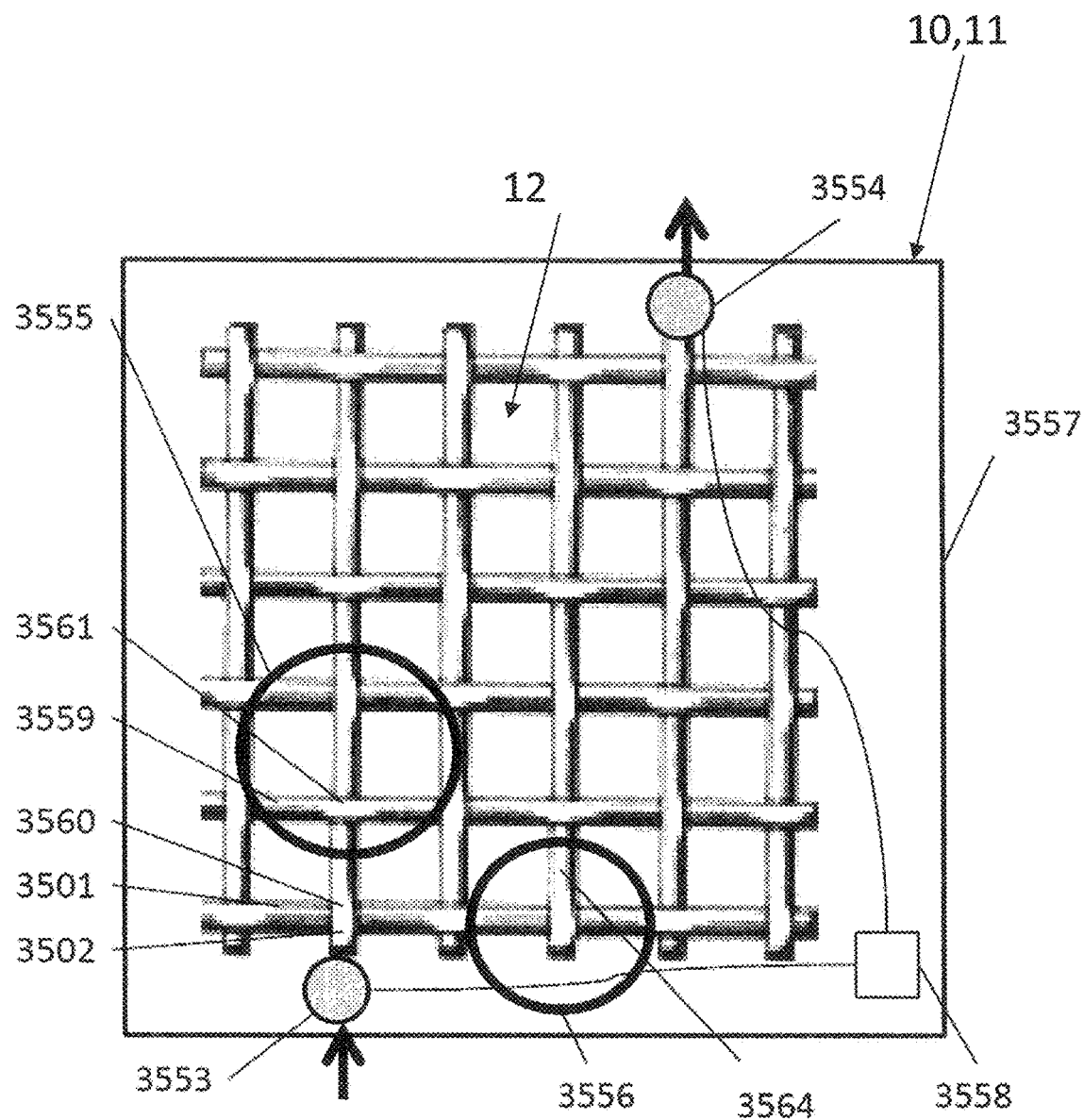

Referring to FIGS. 12 and 13, it is recognized that selected ones of the sensors/actuators 12 can be unidirectional (i.e. used to collect biometric signals representing the data from the wearer) or bidirectional used to apply signals representing to the wearer). As discussed, functionality of the textile based band 10 and/or garment 11 with resident sensors/actuators 12 can cover the body 8 part of the wearer such as but not limited to: waist or abdomen; buttocks; and/or pelvic area. The textile based band 10 and/or garment 11 can be provided as a stand-alone article or can be combined/combined into an article of clothing. The sensors/actuators 12 of the textile based band 10 and/or garment 11 can be formed as an integral component of the interlacing of the fibres making up the body of the textile fabric. The fabric can be comprised of interlaced resilient fibres (e.g. stretchable natural and/or synthetic material and/or a combination of stretchable and non-stretchable materials, recognizing that at least some of the fibres comprising the sensors/actuators 12 are electrically conductive, i.e. metallic).

For example, referring to FIGS. 12 and 13, in one example embodiment, knitting can be used to integrate different sections of the textile (i.e. body fibres incorporating fibres of the sensors/actuators 12) into a common layer (e.g. having conductive pathway(s) and non-conductive sections). Knitting comprises creating multiple loops of fibre or yarn, called stitches, in a line or tube. In this manner, the fibre or yarn in knitted fabrics follows a meandering path (e.g. a course), forming loops above and below the mean path of the yarn. These meandering loops can be easily stretched in different directions. Consecutive rows of loops can be attached using interlocking loops of fibre or yarn. As each row progresses, a newly created loop of fibre or yarn is pulled through one or more loops of fibre or yarn from a prior row. In another example embodiment, can be used to integrate different sections of the textile (i.e. body fibres incorporating fibres of the sensors/actuators 12) into a common layer (e.g. having conductive pathway(s) and non-conductive sections). Weaving is a method of forming a textile in which two distinct sets of yarns or fibres are interlaced at transverse to one another (e.g. right angles) to form a textile.

FIG. 12 shows an exemplary knitted configuration of a network of electrically conductive fibres 3505 in, for example, a segment of an electrically conductive circuit and/or sensor/actuator 12 (see FIG. 1). In this embodiment, an electric signal (e.g. current) is transmitted to conductive fibre 3502 from a power source (not shown) through a first connector 3505, as controlled by a controller 3508 (e.g. controller). The electric signal is transmitted along the electric pathway along conductive fibre 3502 past non-conductive fibre 3501 at junction point 3510. The electric signal is not propagated into non-conductive fibre 3501 at junction point 3510 because non-conductive fibre 3501 cannot conduct electricity. Junction point 3510 can refer to any point where adjacent conductive fibres and non-conductive fibres are contacting each other (e.g. touching). In the embodiment shown in FIG. 12, non-conductive fibre 3501 and conductive fibre 3502 are shown as being interlaced by being knitted together. Knitting is only one exemplary embodiment of interlacing adjacent conductive and non-conductive fibres. It should be noted that non-conductive fibres forming non-conductive network 3506 can be interlaced (e.g. by knitting, etc.). Non-conductive network 3506 can comprise non-conductive fibres (e.g. 3501) and conductive fibres (e.g. 3514) where the conductive fibre 3514 is electrically connected to conductive fibres transmitting the electric signal (e.g. 3502).

In the embodiment shown in FIG. 12, the electric signal continues to be transmitted from junction point 3510 along conductive fibre 3502 until it reaches connection point 3511. Here, the electric signal propagates laterally (e.g. transverse) from conductive fibre 3502 into conductive fibre 3509 because conductive fibre 3509 can conduct electricity. Connection point 3511 can refer to any point where adjacent conductive fibres (e.g. 3502 and 3509) are contacting each other (e.g. touching). In the embodiment shown in FIG. 12, conductive fibre 3502 and conductive fibre 3509 are shown as being interlaced by being knitted together. Again, knitting is only one exemplary embodiment of interlacing adjacent conductive fibres. The electric signal continues to be transmitted from connection point 3511 along the electric pathway to connector 3504. At least one fibre of network 3505 is attached to connector 3504 to transmit the electric signal from the electric pathway (e.g. network 3505) to connector 3504. Connector 3504 is connected to a power source (not shown) to complete the electric circuit.

FIG. 13 shows an exemplary woven configuration of a network of electrically conductive fibres 3555. In this embodiment, an electric signal (e.g. current) is transmitted to conductive fibre 3552 from a power source (not shown) through a first connector 3555, as controlled by a controller 3558 (e.g. controller). The electric signal is transmitted along the electric pathway along conductive fibre 3552 past non-conductive fibre 3551 at junction point 3560. The electric signal is not propagated into non-conductive fibre 3551 at junction point 3560 because non-conductive fibre 3551 cannot conduct electricity. Junction point 3560 can refer to any point where adjacent conductive fibres and non-conductive fibres are contacting each other (e.g. touching). In the embodiment shown in FIG. 13, non-conductive fibre 3551 and conductive fibre 3502 are shown as being interlaced by being woven together. Weaving is only one exemplary embodiment of interlacing adjacent conductive and non-conductive fibres. It should be noted that non-conductive fibres forming non-conductive network 3556 are also interlaced (e.g. by weaving, etc.). Non-conductive network 3556 can comprise non-conductive fibres (e.g. 3551 and 3564) and can also comprise conductive fibres that are not electrically connected to conductive fibres transmitting the electric signal. The electric signal continues to be transmitted from junction point 3560 along conductive fibre 3502 until it reaches connection point 3561. Here, the electric signal propagates laterally (e.g. transverse) from conductive fibre 3552 into conductive fibre 3559 because conductive fibre 3559 can conduct electricity. Connection point 3561 can refer to any point where adjacent conductive fibres (e.g. 3552 and 3559) are contacting each other (e.g. touching). In the embodiment shown in FIG. 13, conductive fibre 3552 and conductive fibre 3559 are shown as being interlaced by being woven together. Again, weaving is only one exemplary embodiment of interlacing adjacent conductive fibres. The electric signal continues to be transmitted from connection point 3561 along the electric pathway through a plurality of connection points 3561 to connector 3554. At least one conductive fibre of network 3555 is attached to connector 3554 to transmit the electric signal from the electric pathway (e.g. network 3555) to connector 3554. Connector 3554 is connected to a power source (not shown) to complete the electric circuit.

In accordance with one or more of the embodiments, the body layer of the band 10 and/or garment 11 can be made on a seamless knitting machine where the electrical circuit is an integral part of the band 10 and/or garment 11, with identical or similar physical properties (stretch, recovery, weight, tensile strength, flex, etc.). The seamless knitting machine can include a circular knit machine manufactured by the SANTONI™ Company, a flat-bed knit machine manufactured by the SHIMA SEIKI® Company, the seamless warp knit machine, and other seamless garment machines, and any equivalent thereof.

We claim:

1. A resilient material band for use as a waistband of a garment providing a sensor platform for a body of a wearer in order to sense a plurality of biometric data, the band comprising:
    a plurality of insulative fibers interlaced to one another comprising a material of a body of the band, the band having a first centerline extending between a front and a back of the band and a second centerline extending from side to side of the band such that the second centerline defines the front from the back of the body, such that that first centerline and the second centerline are transverse to one another;
    a pair of ECG sensors coupled to an interior surface of a body of the band, each of the pair of ECG sensors respectively located on either side of the first centerline on the front such that each of the pair of ECG sensors is positioned in a respective hip region on the front of the band as the waistband, each of the hip regions positioned adjacent to a respective hip of the wearer at the waist;
    a pair of bio impedance sensors coupled to the interior surface of the body of the band, each of the pair of bio impedance sensors respectively located on either side of the first centerline adjacent to the respective hip region, such that each sensor of the pair of bio impedance sensors are both located on the front of the band to a same side of the second centerline;
    a strain gauge sensor interlaced into the material of the body of the band as a plurality of conductive fibres;
    a first electro-muscular stimulator sensor, the first electro-muscular stimulator sensor positioned in a first location off of the band and in a fabric of the garment towards the back of the band, the first location to one side of the first centerline of the band, the first location adjacent to one or more nerves of pelvic splanchnic nerves of the wearer such that activation of the first electro-muscular stimulator sensor stimulates the one or more nerves of the pelvic splanchnic nerves of the wearer, the fabric of the garment being attached to said band, said first electro-muscular stimulator sensor configured to provide treatment for erectile dysfunction by stimulating the one or more nerves of the pelvic splanchnic nerves of the wearer;
    a computer device mounted on the body of the band via a housing, the computer device including a power source, a computer processor, a memory for storing instructions for execution by the computer processor, and a network interface for transmitting data sensed by the sensors; and
    a plurality of communication pathways connecting the computer device to each of the sensors, the communication pathway for sending power from the power supply to the sensors as controlled by the computer processor and for receiving sensed data from the sensors by the computer processor,
    wherein said computer device is configured to process data received from said strain gauge to determine real-time breathing of said wearer and a posture of said wearer.

2. The band of claim 1 further comprising a temperature sensor mounted in or external to the housing and facing the interior surface of the body.

3. The band of claim 1, wherein the garment is underwear and the band is positioned at the waist of the underwear.

4. The band of claim 1 further comprising motion sensors selected from the group consisting of accelerometer and gyroscope.

5. The band of claim 1, wherein the communication pathways are conductive fibers interlaced in the material of the body of the band.

6. The band of claim 1, further comprising a second electro-muscular stimulator sensor positioned in a second location off of the band and in the fabric of the garment towards the back of the band, said second location being on an opposite side of the first centerline than the first location of the first electro-muscular stimulator sensor, said first and second locations being towards the back of the band and adjacent to the one or more nerves of the pelvic splanchnic nerves of the wearer such that activation of the second electro-muscular stimulator sensor stimulates the one or more nerves of the pelvic splanchnic nerves of the wearer, said first and second electro-muscular stimulator sensors are located on said same side of the second centerline, said second electro-muscular stimulator sensor being configured to provide treatment for erectile dysfunction by stimulating the one or more nerves of the pelvic splanchnic nerves of the wearer.

* * * * *